US008160721B2

(12) United States Patent  
Cooke et al.

(10) Patent No.: US 8,160,721 B2  
(45) Date of Patent: Apr. 17, 2012

(54) IMPLANTABLE LEAD WITH FLEXIBLE TIP FEATURES

(75) Inventors: Daniel J. Cooke, Roseville, MN (US); Leslie J. Carion, White Bear Lake, MN (US); Shrojalkumar Desai, Little Canada, MN (US); Brendan E. Koop, Coon Rapids, MN (US); Ronald W. Heil, Jr., Roseville, MN (US); Harshad M. Borgaonkar, Blaine, MN (US); Matthew S. Finlay, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 377 days.

(21) Appl. No.: 12/508,322

(22) Filed: Jul. 23, 2009

(65) Prior Publication Data

US 2010/0042195 A1 Feb. 18, 2010

Related U.S. Application Data

(60) Provisional application No. 61/089,076, filed on Aug. 15, 2008.

(51) Int. Cl.
*A61N 1/00* (2006.01)
(52) U.S. Cl. ..................................................... 607/126
(58) Field of Classification Search .................. 607/126, 607/127
See application file for complete search history.

(56) References Cited

U.S. PATENT DOCUMENTS

| | | |
|---|---|---|
| 3,974,834 A | 8/1976 | Kane |
| 4,201,815 A | 5/1980 | Weiland et al. |
| 4,667,686 A | 5/1987 | Peers-Travarton et al. |
| 4,924,881 A | 5/1990 | Brewer |
| 4,957,118 A | 9/1990 | Erlebacher |
| 5,002,067 A | 3/1991 | Berthelsen et al. |
| 5,003,992 A | 4/1991 | Holleman et al. |
| 5,246,014 A | 9/1993 | Williams et al. |
| 5,403,295 A | 4/1995 | Byrne |
| 5,545,206 A | 8/1996 | Carson |
| 5,658,326 A | 8/1997 | Barsne |
| 5,658,327 A | 8/1997 | Altman et al. |
| 5,755,767 A | 5/1998 | Doan et al. |
| 5,837,007 A | 11/1998 | Altman et al. |
| 5,868,741 A | 2/1999 | Chia et al. |
| 5,902,329 A | 5/1999 | Hoffmann et al. |
| 5,931,864 A | 8/1999 | Chastain et al. |
| 5,951,597 A | 9/1999 | Westlund et al. |
| 6,161,029 A | 12/2000 | Spreigl et al. |

(Continued)

FOREIGN PATENT DOCUMENTS

EP  0 057 877 B1  7/1985

(Continued)

*Primary Examiner* — George Manuel (74) *Attorney, Agent, or Firm* — Faegre Baker Daniels LLP (57) ABSTRACT

A medical electrical lead comprises a flexible, elongate lead body extending along a longitudinal axis and having a proximal end and a distal end. A protective distal tip structure is disposed on the distal end of the lead body. The tip structure includes a plurality of compliant projections each extending distally from the distal end of the body in the direction of the longitudinal axis. The projections are configured to contact and bear against cardiac tissue when the lead is implanted, and are deformable under the action of an axially or radially directed force. The projections optionally include a coating over a substrate. The coating can include a hydrogel material and/or a pharmaceutical agent such as a steroid for reducing inflammation at the implantation site.

23 Claims, 4 Drawing Sheets

U.S. PATENT DOCUMENTS

| | | |
|---|---|---|
| 6,185,464 B1 | 2/2001 | Bonner et al. |
| 6,360,129 B1 | 3/2002 | Ley et al. |
| 6,370,434 B1 | 4/2002 | Zhang et al. |
| 6,501,990 B1 | 12/2002 | Sundberg et al. |
| 6,695,793 B2 * | 2/2004 | Brennan et al. ............... 600/585 |
| 6,697,677 B2 | 2/2004 | Dahl et al. |
| 6,842,648 B2 | 1/2005 | Partridge et al. |
| 6,901,288 B2 | 5/2005 | Janke et al. |
| 2002/0147487 A1 | 10/2002 | Sundquist et al. |
| 2003/0028224 A1 | 2/2003 | McVenes et al. |
| 2003/0144719 A1 | 7/2003 | Zeijlemaker |
| 2004/0230281 A1 | 11/2004 | Heil et al. |
| 2005/0070986 A1 | 3/2005 | Tockman et al. |
| 2005/0085885 A1 | 4/2005 | Janke et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0186244 A1 | 8/2005 | Hunter et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2006/0095077 A1 | 5/2006 | Tronnes |
| 2006/0095078 A1 | 5/2006 | Tronnes |
| 2006/0247749 A1 | 11/2006 | Colvin |
| 2007/0050003 A1 | 3/2007 | Zarembo et al. |
| 2007/0142890 A1 | 6/2007 | Zarembo et al. |
| 2007/0208402 A1 | 9/2007 | Helland et al. |

FOREIGN PATENT DOCUMENTS

| | | |
|---|---|---|
| EP | 0 618 822 | 10/1994 |
| EP | 0 546 414 B1 | 4/1997 |
| EP | 0 779 080 B1 | 5/2003 |
| EP | 0 761 254 B1 | 11/2003 |

* cited by examiner

IMPLANTABLE LEAD WITH FLEXIBLE TIP FEATURES

CROSS-REFERENCE TO RELATED APPLICATION

This application claims the benefit of Provisional Application No. 61/089,076, filed Aug. 15, 2008, entitled "IMPLANTABLE LEAD WITH FLEXIBLE TIP FEATURES," which is herein incorporated by reference in its entirety.

TECHNICAL FIELD

The present invention relates generally to implantable medical electrical leads, and more particularly, to leads having stabilizing features to facilitate securing the leads to the human anatomy.

BACKGROUND

Various types of medical electrical leads for use in cardiac rhythm management systems are known. Such leads typically extend intravascularly to an implantation location within or on a patient's heart, and thereafter coupled to a pulse generator or other implantable device for sensing cardiac electrical activity, delivering therapeutic stimuli, and the like. The lead typically includes one or more electrodes at or near their distal tip, which electrodes are configured to contact the adjacent cardiac tissue for effective stimulation.

SUMMARY

The present invention, in one embodiment, is a medical electrical lead comprising an elongated lead body and a protective distal tip structure. The body extends along a longitudinal axis and has a proximal end and a distal end. The protective distal tip structure is located on the distal end of the lead body, and includes a plurality of compliant projections each extending distally from the distal end of the body and substantially parallel to the longitudinal axis when in an undeformed state. The projections are configured to bear against cardiac tissue when the lead is implanted, and are deformable under the action of an axially or radially directed force. In one embodiment, at least one projection includes a substrate and a coating covering substantially the entire substrate.

In another embodiment, the present invention is a medical electrical lead comprising an elongate lead body, a protective distal tip structure, and an electrode. The lead body extends along a longitudinal axis and has a proximal end and a distal end, and the electrode is coupled to the distal end of the lead body. The protective distal tip structure is located on the distal end of the lead body and includes a plurality of compliant projections each extending distally from the distal end of the body beyond the electrode and substantially parallel to the longitudinal axis when in an undeformed state. The projections are configured to bear against cardiac tissue when the lead is implanted, and are deformable under the action of an axially or radially directed force. At least one projection includes a hydrogel material configured to swell upon exposure to body fluids.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives failing within the scope of the invention as defined by the appended claims.

DETAILED DESCRIPTION

Figure 1:
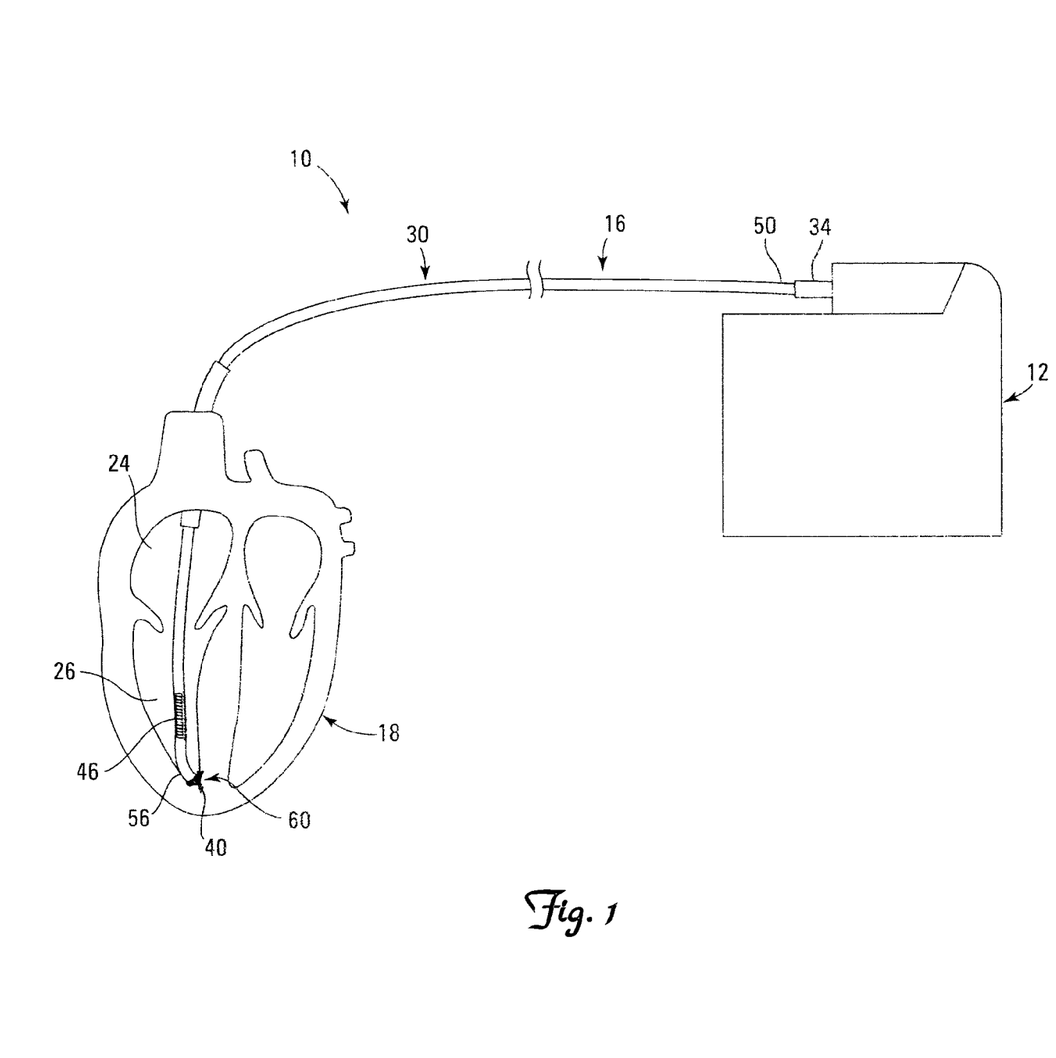
FIG. 1 is a schematic view of a cardiac rhythm management (CRM) system including a pulse generator and medical electrical lead according to an embodiment of the present invention.

FIG. 1 is a schematic view of a cardiac rhythm management (CRM) system 10 according to an embodiment of the present invention. As shown in FIG. 1, the CRM system 10 includes a pulse generator 12 coupled to an implantable medical electrical lead 16 deployed in a patient's heart 18, which includes a right atrium 24 and a right ventricle 26. In the illustrated embodiment, the lead 16 is implanted in the right ventricle 26. In other embodiments, the CRM system 10 may include additional leads, e.g., a lead implanted in the right atrium 24 and/or a lead extending into a coronary vein for stimulating the left ventricle in a bi-ventricular pacing or cardiac resynchronization therapy system.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardiac defibrillator, a cardiac resynchronization (CRT) device configured for bi-ventricular pacing, and/or includes combinations of pacing, CRT, and defibrillation capabilities.

The lead 16 (and additional leads when present) operates to convey electrical signals and stimuli between the heart 18 and the pulse generator 12. As shown in FIG. 1, the lead 16 includes a flexible, elongated body 30, a proximal connector 34, a helical distal tip electrode 40, and a coil electrode 46. As further shown, the lead body 30 has a proximal end 50 coupled to the connector 34, and a distal end 56 positioned, in the implanted configuration shown in FIG. 1, in contact with or at least proximate to cardiac tissue within the right ventricle 26. In the illustrated embodiment, the distal tip electrode 40 is in the form of a fixation helix configured to extend distally with respect to the distal end 56 of the lead body so as to penetrate into the cardiac tissue. As such, the helical tip electrode 40 operates both as an electrode for sensing cardiac rhythm signals and delivering electrical stimuli (generated in the pulse generator 12) to the cardiac tissue, as well as a fixation mechanism for securing the lead 16 in its implanted position.

The coil electrode 46 is coupled to the lead body 30 at a location proximal to the lead body distal end 56. The coil electrode 46 has a relatively large surface area compared to the helical tip electrode 40. In the illustrated embodiment, the coil electrode 46 is configured for delivering relatively high voltage electrical stimulus to the cardiac tissue for defibrillation/cardioversion therapy, while the helical tip electrode 40 is configured as a relatively low voltage pace/sense electrode. In various embodiments, the lead 16 includes additional defibrillation/cardioversion and/or additional pace/sense electrodes positioned along the lead body 30 so as to provide multi-polar defibrillation/cardioversion and/or pacing capabilities. In one exemplary embodiment, the lead 16 includes a proximal coil electrode in addition to the coil electrode 46 positioned along the lead body 30 such that it is located in the right atrium 24 (and/or superior vena cava) when implanted, and further includes a ring electrode located proximal to the helical distal tip electrode 40, which can operate as an anode in a bi-polar pace/sense configuration. In various embodiments, the lead 16 includes one or more additional electrodes, e.g., solid ring electrodes, located near the distal end 56 but proximal to the tip electrode 40. As will be appreciated, such electrodes operate as pacing and/or sensing electrodes, and can be included in addition to or in lieu of the one or more coil electrodes 46, depending on the intended application of the lead 16. In short, any electrode configuration can be employed in the lead 16 without departing from the intended scope of the present invention.

As will be appreciated, each electrode is electrically coupled to a conductive member (not shown in FIG. 1) extending along the lead body, which conductor(s) electrically couple the respective electrodes to contacts in the proximal connector 34. The conductors thus carry electrical current and signals between the pulse generator 12 and the respective electrodes.

As further shown in FIG. 1, the lead 16 includes a protective distal tip structure 60 on the distal end 56 of the lead body 30. As will be explained in further detail below, the protective distal tip structure 60 provides a cushioning and stabilizing effect to the lead 16 upon implantation. The distal tip structure 60 thus provides chronic stability to the lead 16 to improve lead performance and to reduce stresses on the tissue at the implantation site. The distal tip structure 60 also provides, in various embodiments, a platform to which active coatings, e.g., steroids or other bio-beneficial coatings, can be applied.

Figure 2A:
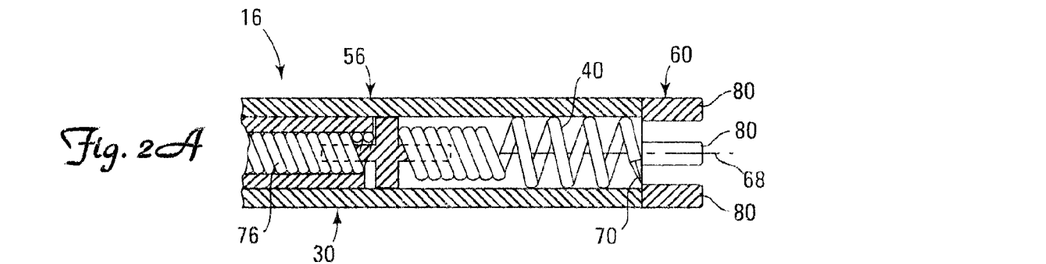
FIGS. 2A and 2B are schematic illustrations of a portion of the lead of FIG. 1 before and after securing the lead to cardiac tissue.
Figure 2B:
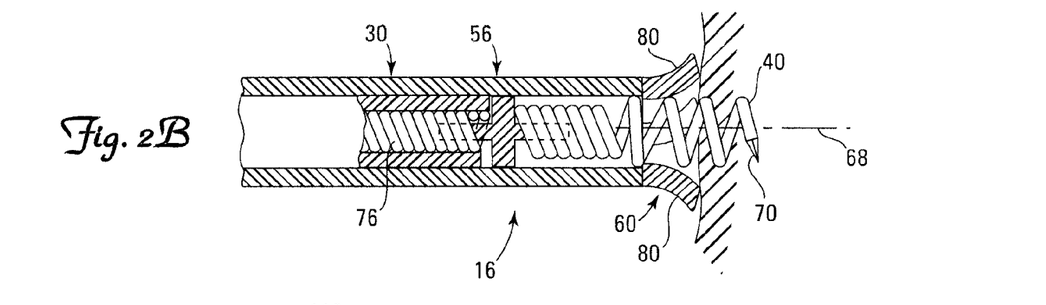

FIGS. 2A and 2B are schematic partial cross-sectional illustrations of a portion of the lead 16, and in particular, of the lead body distal end 56 before and after securing the helical tip electrode 40 to cardiac tissue. As shown in FIGS. 2A and 2B, in the illustrated embodiment, the helical tip electrode 40 is an extendable/retractable helix and thus operable between retracted (FIG. 2A) and extended (FIG. 2B) states generally along a longitudinal axis 68 of the lead 16. As further shown, the helical tip electrode 40 includes a sharpened distal tip 70. In the retracted state of FIG. 2A, the helical tip electrode 40, including the distal tip 70, is disposed substantially or entirely within the lead body 30, while in the extended state illustrated in FIG. 2B, a portion of the tip electrode 40, and in particular, the distal tip 70, extends distally with respect to the distal end 56 of the lead body 30.

In the illustrated embodiment, the distal tip 70 of the tip electrode 40 is disposed entirely within the lead body 30 in the retracted state. In various other embodiments, however, the distal tip 70 may be configured to extend slightly distally beyond the lead body distal end 56 when in the retracted state so as to facilitate, for example, mapping cardiac tissue for selection of an appropriate implantation site.

The helical tip electrode 40 is operable between the extended and retracted states through relative rotation of the tip electrode 40 and the lead body 30. In the illustrated embodiment, the lead 16 includes a coil conductor 76 operatively coupled to the helical tip electrode 40. As will be appreciated, the coil conductor 76 extends longitudinally within the lead body 30 to a rotatable terminal pin (not shown) of the proximal connector 34 (see FIG. 1), and is rotatable within the lead body 30 in response to rotation of the terminal pin relative to the lead body 30. Rotation of the coil conductor 76 is transmitted to the helical tip electrode 40, and a mechanism or structure within the distal end 56 of the lead body 30 causes the helical tip electrode 40 to translate longitudinally relative to the lead body 30 as the tip electrode 40.

Various mechanisms for facilitating extension and retraction of helical tip electrodes and/or fixation helixes for implantable leads are known in the art. By way of example only, extendable/retractable helix structures such as described in commonly assigned U.S. Pat. No. 6,501,990, which is incorporated herein by reference in its entirety for all purposes, can be utilized to facilitate relative rotation of the tip electrode 40 with respect to the lead body 30. In other embodiments, the helical tip electrode 40 can be extended and retracted using a tool deployable through the lead body 30, e.g., a stylet, having a distal end configured to engage a feature on the helical tip electrode 40. Various such structures are known in the art and thus are not discussed in detail herein. It is emphasized, however, that any mechanism or technique for facilitating rotation and extension/retraction of the tip electrode 40, whether now known or later developed, can be utilized in the lead 16.

The various components of the lead 16, e.g., the lead body 30 and the helical tip electrode 40, can be made from any materials, whether now known or later developed, suitable for implantable medical electrical leads. In various embodiments, for example, the lead body 30, or at least portions thereof, is made from silicone rubber. In various embodiments, the lead body 30 is made from polyurethane. In various embodiments, different portions of the lead body 30 may be made from silicone rubber and polyurethane, respectively. Of course in still other embodiments, other materials may be utilized for the lead body 30. In one embodiment, the lead body 30 may include a portion at the distal end 56 operating as a housing for the helical tip electrode 40, which portion may be made of a different material than the adjacent portions of the lead body 30.

The protective distal tip structure 60 includes a plurality of compliant projections 80 each extending distally from the distal end 56 of the lead body 30. The projections 80 are configured to contact and bear against cardiac tissue when the lead 16 is implanted. As shown in FIGS. 2A and 2B, in an un-deformed state, the projections 80 extend in the direction of and substantially parallel to the longitudinal axis 68 of the lead 16, and are deformable under forces imposed by the cardiac tissue, e.g., when the helical tip electrode 40 is advanced into the tissue and subsequently under natural motion of the heart. The projections 80 thus operate to provide a cushioning effect at the implantation site. The projections 80 also increase the contact surface area between the lead 16 and the cardiac tissue, which in turn enhances the ability of any pharmaceutical substances, e.g., steroids, applied to the projections 80 to interact with the adjacent tissue. Thus, the projections 80 operate, in part, to reduce tissue irritation and also to enhance mechanical compatibility between the native cardiac tissue and the implanted lead 16 at the interface between the two.

In various embodiments, the stiffness and/or compliance of the distal tip structure 60, and in particular the projections 80, are tailored according to the particular therapeutic needs of the patient. In various embodiments, the projections 80 are configured to generally match the stiffness and/or compliance of the adjacent cardiac tissue upon which the projections 80 bear when implanted. In various embodiments, the projections 80 are configured to be relatively soft and compliant relative to the adjacent distal end 56 of the lead body 30. In various embodiments, the projections 80 are configured to exhibit stiffness and/or compliance between that of the relatively stiff lead body distal end 56 and the adjacent cardiac tissue. Tailoring the stiffness and compliance of the projections 80 can be accomplished, for example, through selection of the physical dimensions and/or shapes of the projections 80, material selection, and/or combinations of the two.

In light of the foregoing considerations, the protective distal tip structure 60, including the projections 80, can be made of any materials, whether now known or later developed, providing the desired stiffness and compliance characteristics. In various embodiments, the projections 80 are made of silicone rubber. In various embodiments, the projections 80 are made of other materials, e.g., polyurethane or other suitable, biocompatible materials, including, without limitation, co-polymers of silicone and/or polyurethane. As will be appreciated, the foregoing materials can be provided in a range of durometers, so as to provide wide flexibility in the stiffness and compliance of the projections 80.

In various embodiments, one or more of the projections 80 are made of natural, synthetic, or hybrid biocompatible polymers, including hydrogel materials formulated to incorporate water into their structures and thereby swell (longitudinally and/or radially) and provide a soft contacting surface with increased surface area at the interface between the lead and the native cardiac tissue. Exemplary suitable synthetic hydrogels that can be utilized for the projections 80 include, but are not limited to, polyvinylacohol, polyvinylacetate, polyhydroxyethyl methacrylate (pHEMA), polyN-isopropylalcohol, polyethylene glycol (PEG), polyethylene glycol methacrylate, polyvinylpyrrolidone, hydrolyzed polyacrylonitrile, polyacrylamide, and copolymers of the foregoing, either cross-linked or not cross-linked. Exemplary natural polymers that will form suitable hydrogel materials for the projections 80 include, but are not limited to, chitosan, hyaluranon, collagen, Matrigel™, gelatin, alginate, hydroxyapatite, and glycosaminoglycan, also either cross-linked or not cross-linked. In various embodiments, for example, PEG-, HEMA- or hylauronan-based cross-linked hydrogels are utilized to form the projections 80 to provide enhanced cushioning effects when implanted. In various embodiments, the foregoing materials may also include and/or be coated with materials having enhanced tissue-healing properties, including without limitation, pro-healing peptides such as arginine-glycine-aspartate (RGD) and GOFOGER peptides, which may further enhance tissue healing and, in turn, lead fixation. Of course, still other suitable hydrogel materials that can be used to form the projections 80 will be apparent to those skilled in the art based on the foregoing.

The parameters of the projections 80 can be tailored to achieve the desired effect. Such parameters can include, without limitation, the material properties and dimensions of the projections 80. In embodiments in which the projections 80 are made from or include a hydrogel material, the hydrogel chemistry or other hydrogel parameters can be tailored for the desired effect. In one embodiment, for example, different hydrogels are utilized for respective projections 80, such that the respective projections 80 have varying expanded properties. In such embodiments, the expanded shape of the protective tip structure 60 can be varied to achieve a wide range of functionality. For example, the distal tip structure 60 can be configured such that some projections 80 expand to a greater degree than others. As a result, the distal tip structure 60, which contacts and bears against the cardiac tissue surface post-implantation, will have an asymmetric profile. This in turn may tend to urge the lead body 30 to a desired shape for chronic implantation. Other desirable variations in the configuration of the projections 80 will be apparent to those skilled in the art based on the foregoing.

In various embodiments, the projections 80 include surface treatments and/or coatings to provide desired characteristics including, without limitation, enhanced tissue response, enhanced healing response, enhanced fixation, and the like. For example, in various embodiments, the projections 80 may be plasma-treated to provide either a relatively rough surface or, if desired, a highly lubricious surface. In some embodiments, the projections may be covered with a porous material, e.g., expanded polytetrafluoroethylene (ePTFE) configured to promote or inhibit (depending on the selected pore size) tissue ingrowth. Additional coatings for the projections 80 may be utilized, depending on the desired functional characteristics.

The distal tip structure 60, including the projections 80, can be integrally formed with all or portions (e.g., the distal end 56) of the lead body 30, or may be separately formed and attached to the lead body distal end 56 using any suitable technique, e.g., adhesive bonding, polymer welding, heat fusion, and the like. For example, in one embodiment, the lead body 30, or at a minimum, the distal end 56 of the lead body 30, and the distal tip structure 60 including the projections 80 are integrally formed as an extrusion of silicone rubber (or other suitable material). In another embodiment, the distal end 56 of the lead body includes a housing (not shown) for the helical tip electrode 40 and associated extension/retraction mechanism, which housing may be made from a relatively hard material such as polyetheretherketone (PEEK™), and the distal tip structure 60 is separately attached to this housing.

In various embodiments, the distal tip structure includes a base portion from which the projections 80 extend, which may advantageously facilitate attachment of the distal tip structure 60 to the lead body distal end 56. In still other embodiments, the projections 80 are attached directly to the lead body distal end 56. Still other techniques and configurations for forming the lead body distal end 56 and the distal tip structure 60 will be apparent to those skilled in the art.

Figure 3A:
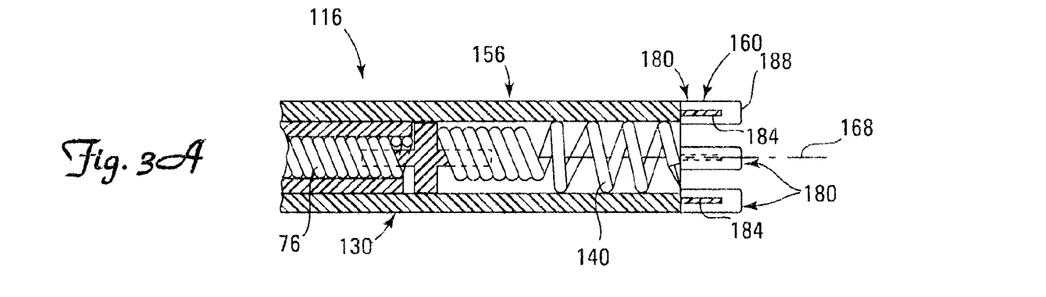
FIGS. 3A and 3B are schematic illustrations of portions of an alternative lead suitable for use in the CRM system of FIG. 1 according to various embodiments of the present invention.
Figure 3B:
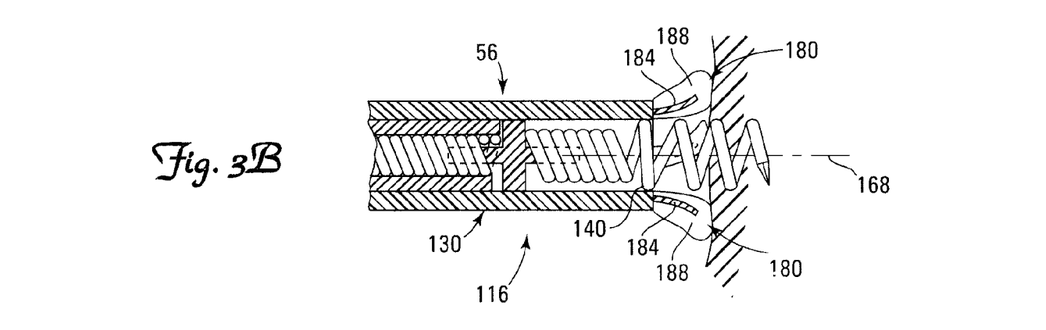

FIGS. 3A and 3B are schematic illustrations of a portion an alternative lead 116 suitable for use in the CRM system of FIG. 1 according to various embodiments of the present invention. The lead 116 is, except has discussed below, of generally the same design and construction of the lead 16 discussed above, and includes a lead body 130 and a helical tip electrode 140. The lead body 130 has a distal end 156, and the helical tip electrode is retractable substantially within and extendable from the distal end 156 of the lead body 130 in the same manner as described above with respect to the lead 16.

As further shown in FIGS. 3A and 3B, the lead 116 includes a protective tip structure 160 including a plurality of relatively soft, compliant projections 180 extending distally from the distal end 156 of the lead body 130. The projections 180 include a substrate 184 and a coating 188 designed to enhance the performance of the tip structure 160. In the illustrated embodiment, the coating 188 is a polymer coating including a hydrogel material specifically formulated to swell upon exposure, for a sufficient time period, to a water-containing fluid, e.g., blood. The projections 180 are thus configured to expand and enlarge after deployment of the lead body distal end 156 in the heart 18.

Inclusion of the hydrogel-containing coating 188 on the projections 180 permits the projections 180 to be relatively small and low-profile (see FIG. 3A) prior to and during deployment of the lead 116 in the heart 18. The reduced-profile pre-deployment dimensions facilitate ease of delivery, e.g., by allowing the use of a relatively small-diameter sheath introducer or catheter and by minimizing the potential for interference with the patient's vascular anatomy during deployment. Upon deployment and sufficient exposure to blood and/or other bodily fluids, the hydrogel-containing coating 188 will expand to the desired dimensions for chronic lead cushioning and stabilization (see FIG. 3B). In various embodiments, the hydrogel-containing coating 188 may have adhesive properties and may operate to temporarily attach the projections 180 to one another during lead delivery, further reducing the diameter and/or profile of the protective tip structure 160.

The hydrogel in the coating 188 can have any chemistry, whether now known or later developed, that will provide the sufficient expansion characteristics as well has having the appropriate softness and compliance so as to provide the desired cushioning and lead stabilization effects. Any of the synthetic, natural, or hybrid polymeric hydrogel materials described above in connection with the projections 80 of the lead 16 can be utilized for the coating 188.

The parameters of the coating 188 can be tailored to achieve the desired effect. Such parameters can include, without limitation, the hydrogel chemistry, the quantity of hydrogel in the coating, the coating thickness, and the like. In various embodiments, the coating 188 is applied to a uniform thickness to all of the projections 180. In other embodiments, the coating 180 is applied to different thicknesses on different projections 180. In various embodiments, the coating 188 is not applied to all projections 180. In various embodiments, the coatings 188 applied to different projections 180 can have different chemistries, and in turn, different expansion properties.

By varying the hydrogel-containing coating 188 parameters, e.g., thickness, chemistry, etc., and/or selectively applying the coating 188 to only some of the projections 180, the expanded shape of the protective tip structure 160 can be varied to achieve a wide range of functionality. For example, the coating 188 can be configured such that some projections 180 expand to a greater degree than others. As a result, the distal tip structure 160, which contacts and bears against the cardiac tissue surface post-implantation, will have an asymmetric profile. This in turn may tend to urge the lead body 130 to a desired shape for chronic implantation. Other desirable variations in the configuration of the projections 180 and/or the coating 188 will be apparent to those skilled in the art based on the foregoing.

In some embodiments, the coating 188 is a multi-layer coating. For example, in one embodiment, the coating 188 contains an inner layer adjacent to the substrate 184, and an outer layer over the inner layer. In one embodiment, the inner layer includes a hydrogel and is thus expandable upon sufficient exposure to bodily fluids. The outer layer, on the other hand, includes no hydrogel but instead can be made to be dissolvable upon exposure to body fluids for a predetermined time. In one embodiment, the outer layer is also a lubricious layer. The outer layer thus facilitates ease of delivery by preventing or at least impeding, premature expansion of the hydrogel coating layer, while also reducing the tendency of the lead to catch on the introducer sheath (if used) and/or vascular or cardiac tissue during delivery.

In various embodiments, the coating 188 includes other active constituents in addition to or in lieu of the hydrogel described above. For example, as discussed above, the coating 188 can include bio-compatible or bio-beneficial substances such as steroids or pharmaceutical substances designed to be eluted from the coating at a controlled rate. In various embodiments, the substances in the coating 188 can be designed to improve or speed tissue healing response. In various embodiments, the coating 188 may include nanofibers or nanoparticles designed for a range of desired biological responses. For example, the coating 188 may be configured to promote chronic tissue ingrowth to further improve stability of the lead/tissue contact site.

Figure 4A:
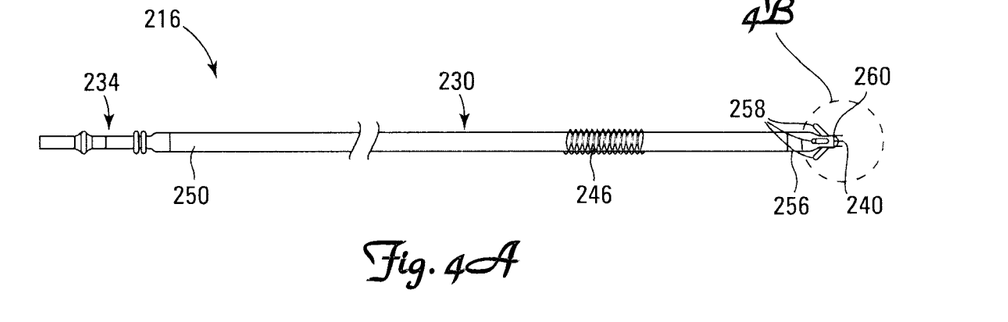
FIGS. 4A and 4B are schematic views of a distal end portion of a passive fixation lead for use in the CRM system of FIG. 1 according to another embodiment of the present invention.
Figure 4B:
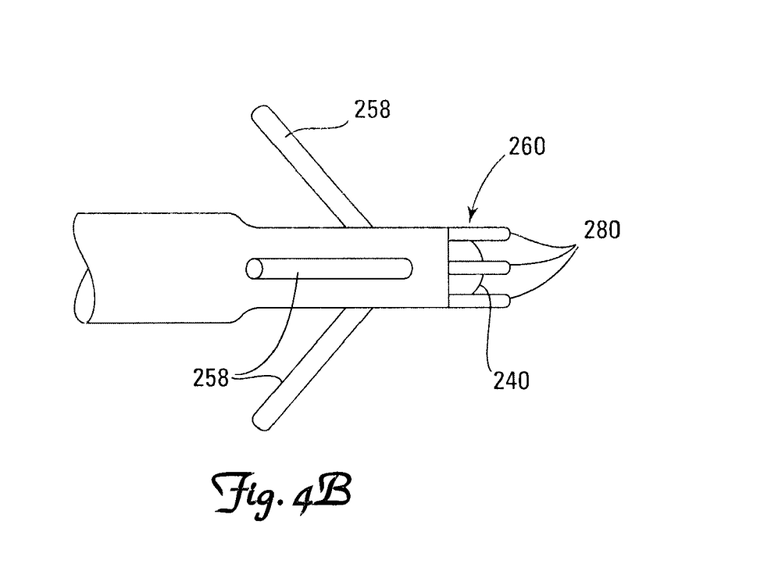

Although FIGS. 2A-2B and 3A-3B illustrate active fixation leads 16, 116 with extendable/retractable helical tip electrodes 80, 180, respectively, those skilled in the art will recognize that the protective tip structures according to the various embodiments of the present invention can also be utilized with fixed-helix active fixation leads. In such leads, as is known, the fixation helix/helical tip electrode is fixedly coupled to the distal end of the lead body FIGS. 4A and 4B are schematic views of a passive fixation lead 216 for use in the CRM system 10 according to another embodiment of the present invention. As shown in FIGS. 4A and 4B, the lead 216 includes a flexible, elongated body 230, a proximal connector 234, a distal tip electrode 240, and a coil electrode 246. As further shown, the lead body 230 has a proximal end 250 coupled to the connector 234, a distal end 256 to which the tip electrode 240 is coupled, and a plurality of resilient tines 258 extending radially outwardly from the major surface of the lead body 230 near the distal end 256. As is known, the tines 258 provide a passive fixation scheme by engaging anatomical features, e.g., trabeculae, other fibrous tissues, or the heart wall itself, to resist spontaneous displacement of the lead 216 from its implanted position. In various embodiments, the lead 216 includes additional pace/sens (e.g., ring) electrodes located proximal to the tip electrode 240. As will be appreciated, in various embodiments, the coil electrode 246 may be omitted.

As further shown in FIGS. 4A and 4B, the lead 216 includes a protective tip structure 260, which in turn includes a plurality of compliant projections 280 each extending distally from the distal end 256 of the lead body 230. The projections 280 are configured to contact and bear against cardiac tissue when the lead 216 is implanted, just as are the projections 80, 180 of the leads 16, 116, respectively. As such, the distal tip structure 160, and in particular, the projections 180, can have any of the configurations or features, including the coatings, described above with respect to the projections 80, 180. Thus, in various embodiments of the present invention, the protective tip structures described herein can be utilized with passive fixation leads as well as active-fixation leads.

Figure 5A:
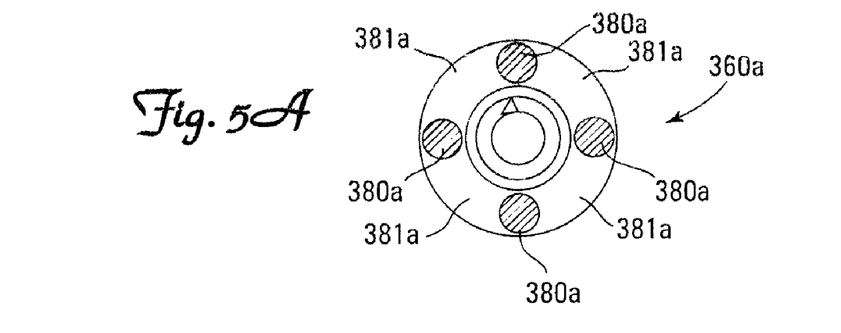
FIGS. 5A-5D illustrate various protective distal tip structures for leads used in the CRM system of FIG. 1 according to additional embodiments of the present invention.

FIGS. 5A-5D are schematic end-view illustrations of protective distal tip structures 360 and corresponding projections 380 which can be utilized in any of the leads 16, 116, and 216 according to various embodiments of the present invention. FIG. 5A illustrates a distal tip structure 360a including a plurality of projections 380a each having a generally circular transverse cross-sectional shape. As shown, the projections 360a are arranged generally in a circle with a gap 381a between adjacent projections 380a. In various other embodiments, one, more, or all of the projections 380a can have elliptical or other non-circular, non-polygonal transverse cross-sectional shapes.

Figure 5B:
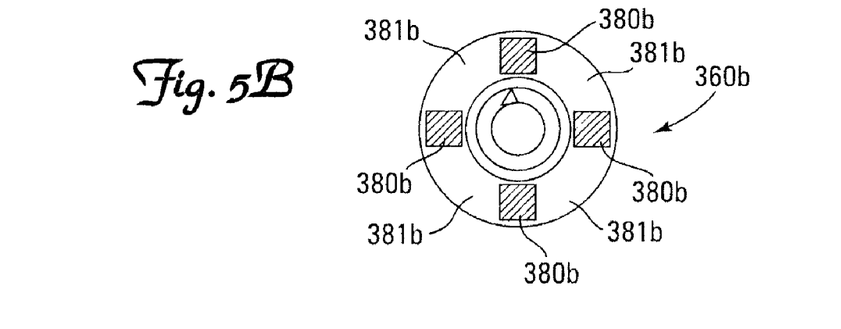

FIG. 5B illustrates a distal tip structure 360a including a plurality of projections 380b having a generally square transverse cross-sectional shape. As shown, the projections 38ba are arranged generally in a circle with a gap 381b between adjacent projections 380b. Of course, in various embodiments, one, more, or all of the projections 380b may have non-square rectangular cross-sectional shapes. In still other embodiments, one, more, or all of the projections 380b may have other polygonal transverse cross-sectional shapes.

Of course, the projections 380a, 380b need not be confined to the perimeter of the protective tip structure 360a, 360b, but can also occupy other positions. Additionally, as discussed above, the respective projections 380a, 380b need not have the same dimensions or shapes on any particular lead.

Figure 5C:
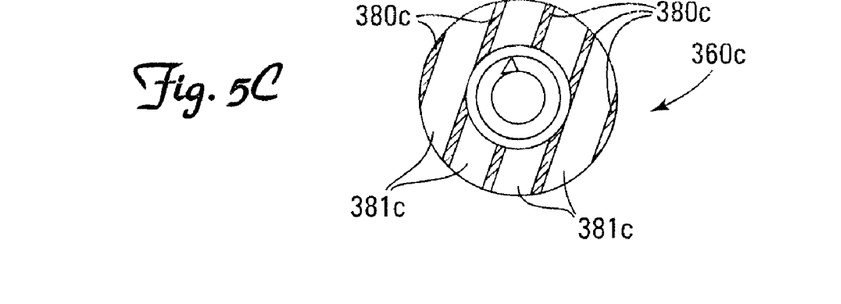
Figure 5D:
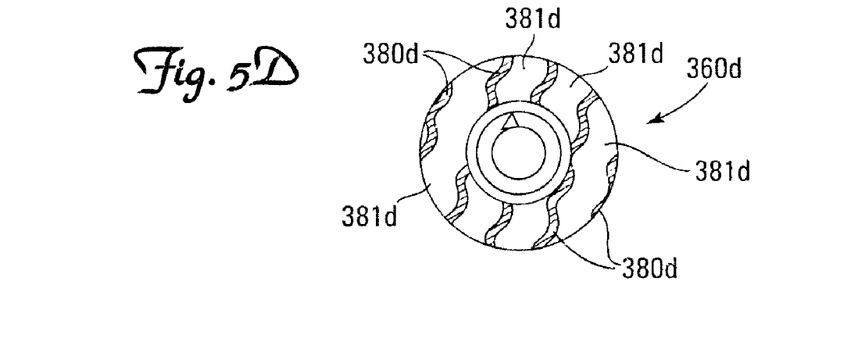

FIGS. 5C and 5D illustrate additional alternative distal tip structures 360c, 360d, each including, respectively, a plurality of projections 380c, 380d separated by elongated transverse slots 381c, 381d. In the embodiment of FIG. 5C, the slots 381c are generally straight, whereas in FIG. 5D, the slots 381d are curved. The slots 381c, 381d thus form gaps between adjacent projections 380c, 380d, respectively. In various embodiments, for example, the projections 380c, 380d can be formed by cutting or etching the slots in a solid disk of material. As discussed above in connection with the lead 16, the projections 380c, 380d can be integrally formed with the respective lead body, or can be separately formed and attached using a suitable joining technique.

The projections 380a-380d and the respective gaps 381a-381d provide extended surfaces and in turn, increased surface areas as compared to a lead lacking the protective tip structures 360a-360d. These extended surfaces can advantageously serve as surfaces for receiving any of the functional coatings described above. Such coatings may be selected to provide a wide range of functions, including without limitation, promoting or inhibiting tissue in growth, inhibiting inflammation and associated threshold increases, improving tissue healing response, and the like. Active components of the coatings can include, for example, anti-inflammatory substances (e.g., steroids such as dexamethasone), nanoparticles (which may be loaded with drugs and/or growth factors), hydrophilic or other lubricious substances, and/or substances to accelerate fibrotic formation. Of course, the coatings can also include a hydrogel material configured to expand upon sufficient exposure to body fluids, as described above.

In various embodiments, the extended and increased surfaces formed by the projections 380a-380d can also be directly treated, e.g., by a plasma-treating process, to provide a desired functionality. For example, the projections 380a-380d can be treated to include surface features designed to mechanically interact with the contacted cardiac tissue to resist spontaneous movement of the projections relative to the tissue. Such treatments can be performed in addition to or in lieu of the coatings described above.

Additionally, the gaps 381a-381d between the respective projections 380a-380d form, in effect, wells that can receive a filler material containing the active substances described above. For example, in various embodiments, the filler material can include a hydrogel material and/or a pharmaceutical substance such as those described above with respect to the various coatings applicable on the projections. Such filler materials can be provided in lieu of or in addition to the coatings described above. In various embodiments, the filler materials may be configured to be softer and more compliant than the corresponding projections 380a-380d so as to not adversely affect the lead cushioning and stabilization performance of the protective tip structure.

Again, any of the distal tip structures 360a, 360b, 360c, and 360d illustrated in FIGS. 5A-5D and described in the accompanying text can be utilized in conjunction with the leads 16, 116, and 216 discussed above. It is emphasized, however, that the particular protective distal tip structure and projection configurations and shapes shown in FIGS. 5A-5D are exemplary only. Thus, any projection shape and configuration providing the desired cushioning and lead stabilization effects are intended to be within the scope of the embodiments of the present invention.

Modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead comprising:
an elongated lead body extending along a longitudinal axis and having a proximal end and a distal end; and
a protective distal tip structure on the distal end of the lead body, the tip structure including a plurality of compliant projections each extending distally from the distal end of the body and substantially parallel to the longitudinal axis when in an undeformed state, the projections configured to bear against cardiac tissue when the lead is implanted, wherein the projections are deformable under the action of an axially or radially directed force, the projections are made of silicone rubber, polyurethane, or co-polymers thereof, and at least one of the projections includes a coating having an active agent.

2. The lead of claim 1 wherein the active agent is configured to promote tissue healing.

3. The lead of claim 1 further comprising a helical electrode terminating in a sharpened distal tip, the helical electrode operable between extended and retracted states, wherein in the retracted state the helical electrode is substantially retracted longitudinally within the lead body, and in the extended state the sharpened distal tip and a length of the helical electrode are located distally beyond the distal end of the lead body, the helical electrode being configured to penetrate cardiac tissue upon rotation of the helical electrode so as to secure the lead thereto with the projections contacting and bearing against the cardiac tissue.

4. The lead of claim 1 further comprising a helical electrode terminating in a sharpened distal tip, the helical electrode fixedly coupled to the distal end of the lead body, the helical electrode being configured to penetrate cardiac tissue upon rotation of the lead body so as to secure the lead thereto with the projections contacting and bearing against the cardiac tissue.

5. The lead of claim 1 wherein the lead includes a tip electrode coupled to the distal end of the lead body, and wherein the projections are disposed circumferentially about the tip electrode.

6. A medical electrical lead comprising:
an elongated lead body extending along a longitudinal axis and having a proximal end and a distal end; and a protective distal tip structure on the distal end of the lead body, the tip structure including a plurality of compliant projections each extending distally from the distal end of the body and substantially parallel to the longitudinal axis when in an undeformed state, the projections configured to bear against cardiac tissue when the lead is implanted, wherein the projections are deformable under the action of an axially or radially directed force, and the projections are made substantially from a biocompatible polymeric material including a hydrogel configured to swell upon exposure to body fluids.

7. The lead of claim 6 wherein at least one of the projections includes a coating having an active agent.

8. The lead of claim 7 wherein the active agent is configured to promote tissue healing.

9. A medical electrical lead comprising:
an elongated lead body extending along a longitudinal axis and having a proximal end and a distal end; and
a protective distal tip structure on the distal end of the lead body, the tip structure including a plurality of compliant projections each extending distally from the distal end of the body and substantially parallel to the longitudinal axis when in an undeformed state, the projections configured to bear against cardiac tissue when the lead is implanted, wherein the projections are deformable under the action of an axially or radially directed force, wherein adjacent projections are separated by a gap, and wherein at least one gap is filled with a filler of polymeric material.

10. The lead of claim 9 wherein the polymeric material includes an active agent configured to promote tissue healing.

11. The lead of claim 9 wherein the polymeric material includes a steroid, and wherein the polymeric material is configured to elute the steroid at a controlled rate so as to reduce inflammation proximate the lead electrode.

12. A medical electrical lead comprising:
an elongated lead body extending along a longitudinal axis and having a proximal end and a distal end; and
a protective distal tip structure on the distal end of the lead body, the tip structure including a plurality of compliant projections each extending distally from the distal end of the body and substantially parallel to the longitudinal axis when in an undeformed state, the projections configured to bear against cardiac tissue when the lead is implanted,
wherein the projections are deformable under the action of an axially or radially directed force, and
wherein at least one projection includes a substrate and a coating covering substantially the entire substrate.

13. The lead of claim 12 wherein the substrate of is made substantially from silicone rubber, polyurethane, or co-polymers thereof.

14. The lead of claim 13 wherein the coating is a polymer material including hydrogel material.

15. The lead of claim 12 wherein the coating is a polymer material including a pharmaceutical substance.

16. The lead of claim 12 further comprising a helical electrode terminating in a sharpened distal tip, the helical electrode operable between extended and retracted states, wherein in the retracted state the helical electrode is substantially retracted longitudinally within the lead body, and in the extended state the sharpened distal tip and a length of the helical electrode are located distally beyond the distal end of the lead body, the helical electrode being configured to penetrate cardiac tissue upon rotation of the helical electrode so as to secure the lead thereto with the projections contacting and bearing against the cardiac tissue.

17. The lead of claim 12 further comprising a helical electrode terminating in a sharpened distal tip, the helical electrode fixedly coupled to the distal end of the lead body, the helical electrode being configured to penetrate cardiac tissue upon rotation of the lead body so as to secure the lead thereto with the projections contacting and bearing against the cardiac tissue.

18. The lead of claim 12 wherein the lead includes a tip electrode coupled to the distal end of the lead body, and wherein the projections are disposed circumferentially about the tip electrode.

19. A medical electrical lead comprising:
an elongated lead body extending along a longitudinal axis and having a proximal end and a distal end;
an electrode coupled to the distal end of the lead body; and
a protective distal tip structure on the distal end of the lead body, the tip structure including a plurality of compliant projections each extending distally from the distal end of the body beyond the electrode and substantially parallel to the longitudinal axis when in an undeformed state, the projections configured to bear against cardiac tissue when the lead is implanted,
wherein the projections are deformable under the action of an axially or radially directed force, and
wherein at least one projection includes a hydrogel material configured to swell upon exposure to body fluids.

20. The lead of claim 19 wherein the at least one projection is made substantially entirely from the hydrogel material.

21. The lead of claim 19 wherein the at least one projection includes a coating over the hydrogel material.

22. The lead of claim 21 wherein the coating includes an active agent configured to promote tissue healing.

23. The lead of claim 19 wherein the at least one projection includes a substrate and a coating covering substantially the entire substrate, wherein the coating includes the hydrogel material.

* * * * *